US009138455B2

(12) United States Patent
Hondmann et al.

(10) Patent No.: US 9,138,455 B2
(45) Date of Patent: *Sep. 22, 2015

(54) ACTIVATING ADIPONECTIN BY CASEIN HYDROLYSATE

(71) Applicant: Mead Johnson Nutrition (Asia Pacific) Pte. Ltd., Singapore (SG)

(72) Inventors: Dirk Hondmann, Winnetka, IL (US);
Eric A.F. van Tol, Arnhem (NL);
Gabriele Gross, Nijmegen (NL);
Marieke H. Schoemaker, Rhenen (NL);
Teartse Tim Lambers, Nijmegen (NL);
Tania Romacho, Düsseldorf (DE);
Manuela Elsen, Düsseldorf (DE);
Jürgen Eckel, Düsseldorf (DE)

(73) Assignee: Mead Johnson Nutrition Company, Glenview, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/839,488

(22) Filed: Mar. 15, 2013

(65) Prior Publication Data

US 2014/0271555 A1    Sep. 18, 2014

(51) Int. Cl.
*A61K 38/01* (2006.01)
*A61K 31/202* (2006.01)
*A61K 45/06* (2006.01)
*A23L 1/305* (2006.01)
*A23J 3/34* (2006.01)
*A23L 1/29* (2006.01)

(52) U.S. Cl.
CPC .............. *A61K 38/018* (2013.01); *A23J 3/344* (2013.01); *A23L 1/296* (2013.01); *A23L 1/3053* (2013.01); *A61K 31/202* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | |
|---|---|---|
| 3,876,766 A | 4/1975 | Frommer et al. |
| 3,937,817 A | 2/1976 | Frommer et al. |
| 4,016,260 A | 4/1977 | Karasaki et al. |
| 4,358,465 A | 11/1982 | Brule et al. |
| 4,361,587 A | 11/1982 | Brule et al. |
| 4,491,589 A | 1/1985 | Dell et al. |
| 4,902,501 A | 2/1990 | Bandi et al. |
| 5,102,871 A | 4/1992 | Furukawa et al. |
| 5,112,812 A | 5/1992 | Samuelsson et al. |
| 5,230,902 A | 7/1993 | Gold et al. |
| 5,308,832 A | 5/1994 | Garleb et al. |
| 5,405,637 A | 4/1995 | Martinez et al. |
| 5,605,893 A | 2/1997 | Kaufman |
| 5,643,880 A | 7/1997 | Mukerji et al. |
| 5,714,472 A | 2/1998 | Gray et al. |
| 5,723,446 A | 3/1998 | Gray et al. |
| 5,821,217 A | 10/1998 | Forse et al. |
| 6,077,558 A | 6/2000 | Euber |
| 6,180,761 B1 | 1/2001 | Han et al. |
| 6,451,368 B1 | 9/2002 | Elliott et al. |
| 6,451,552 B1 | 9/2002 | van Beresteijn et al. |
| 6,468,962 B1 | 10/2002 | Portman |
| 6,495,344 B1 | 12/2002 | Carr et al. |
| 6,713,082 B2 | 3/2004 | van Loon et al. |
| 6,875,456 B2 | 4/2005 | Delest et al. |
| 6,905,702 B1 | 6/2005 | Kaufman |
| 7,022,676 B2 | 4/2006 | Tamura et al. |
| 7,091,320 B2 | 8/2006 | Pozzilli et al. |
| 7,214,521 B2 | 5/2007 | Wada et al. |
| 7,258,996 B2 | 8/2007 | Jullerat et al. |
| 7,501,490 B2 | 3/2009 | Kadowaki et al. |
| 7,550,436 B2 | 6/2009 | Takahashi et al. |
| 7,563,458 B2 | 7/2009 | Kume et al. |
| 7,579,315 B2 | 8/2009 | Smith et al. |
| 7,629,744 B2 | 12/2009 | Ahn et al. |
| 7,648,721 B2 | 1/2010 | Edens et al. |
| 7,648,957 B2 | 1/2010 | Heyden et al. |
| 7,666,996 B2 | 2/2010 | Sidelman |
| 7,741,274 B2 | 6/2010 | Sidelman |
| 7,785,824 B2 | 8/2010 | van der Burg-Koorevaar et al. |
| 7,972,808 B2 | 7/2011 | Edens et al. |
| 8,119,142 B2 | 2/2012 | Zwijsen et al. |
| 8,129,337 B2 | 3/2012 | Wolfram |
| 8,273,710 B2 | 9/2012 | Boots |

(Continued)

FOREIGN PATENT DOCUMENTS

| | | |
|---|---|---|
| CA | 2340223 | 2/2000 |
| DE | 102004040452 | 2/2006 |

(Continued)

OTHER PUBLICATIONS

Hotta (Arterioscler Thromb Vasc Biol (Jun. 2000) 20: 1595-1599).*
Peptide Protein Calculator, http://www.basic.northwestern.edu/biotools/proteincalc.html; downloaded on Jan. 27, 2014.*
Nakamura (Nutrition and Metabolism (2012) 9: 60.).*
Nakamura (Nutrition and Metabolism (2012) 9: 60).*
Wielinga (Mol Nutr Food Res (Jul. 2012) 56(7): 1081-1089).*
Sampson (J Pediatr (1991) 118: 520-525).*
Akuzawa et al (Chapter 8, "Bioactive Components in Caseins, Caseinates, and Cheeses" in Bioactive Components in Milk and Dairy Products, edited by Park (2009) Wiley-Blackwell).*
Ebner et al., "Nonallergic individuals recognize the same T cell epitopes of Bet v 1, the major birch pollen allergen, as atopic patients," J. Immunol. 1995, vol. 154, pp. 1932-1940.
Elsayed et al., "T cell recognition pattern of bovine milk αS1-casein and its peptides," Mol. Immunol. 2004, vol. 41 (12), pp. 1225-1234.
Hirahara et al., K., Profound immunological tolerance in the antibody response against bovine alpha s1-casein induced by intradermal administration of a dominant T cell determinant,: Clinical Immunology and Immunophathology, vol. 76, No. 1, 1995, pp. 12-18.

(Continued)

*Primary Examiner* — Karlheinz R Skowronek
*Assistant Examiner* — Mindy Newman
(74) *Attorney, Agent, or Firm* — Patterson Intellectual Property Law, P.C; James R. Cartiglia; Hilary Dorr Lang

(57) ABSTRACT

The present disclosure provides a method for activating adiponectin by administering a composition comprising peptides selected from a casein hydrolysate. Such a composition may reduce risk of heart attack and help in maintaining healthy weight. Preferably, the hydrolysate consists of peptides with a molecular weight of more than 500 Da.

13 Claims, 1 Drawing Sheet

(56) References Cited

U.S. PATENT DOCUMENTS

| | | | |
|---|---|---|---|
| 8,343,531 B2 | 1/2013 | Morifuji et al. | |
| 8,354,502 B2 | 1/2013 | Recio Sanchez et al. | |
| 8,367,614 B2 | 2/2013 | Hatori et al. | |
| 8,859,210 B2 | 10/2014 | Valenta et al. | |
| 2002/0147144 A1 | 10/2002 | Sidleman | |
| 2003/0138476 A1 | 7/2003 | van Leeuwen et al. | |
| 2004/0063633 A1 | 4/2004 | Hayasawa et al. | |
| 2004/0180380 A1 | 9/2004 | Lee et al. | |
| 2005/0019372 A1 | 1/2005 | Corkey et al. | |
| 2005/0089969 A1 | 4/2005 | Wissler et al. | |
| 2005/0148504 A1 | 7/2005 | Katunuma et al. | |
| 2006/0234942 A1 | 10/2006 | Tauzin et al. | |
| 2007/0031399 A1 | 2/2007 | Edens et al. | |
| 2007/0060519 A1 | 3/2007 | Rozing et al. | |
| 2007/0098762 A1 | 5/2007 | Stahl et al. | |
| 2007/0203060 A1 | 8/2007 | Sidelman et al. | |
| 2008/0031814 A1 | 2/2008 | Hageman | |
| 2008/0075828 A1 | 3/2008 | Wolfram et al. | |
| 2008/0096794 A1 | 4/2008 | Boehm et al. | |
| 2008/0108548 A1 | 5/2008 | Luyer et al. | |
| 2008/0132454 A1 | 6/2008 | Geerlings et al. | |
| 2008/0221023 A1 | 9/2008 | Boots | |
| 2008/0226565 A1 | 9/2008 | Huybrechts | |
| 2009/0036351 A1* | 2/2009 | Boots | 514/2 |
| 2009/0074893 A1 | 3/2009 | de Waard et al. | |
| 2009/0075904 A1 | 3/2009 | Boots | |
| 2009/0123605 A1 | 5/2009 | van Benthum et al. | |
| 2009/0131331 A1 | 5/2009 | Edens et al. | |
| 2009/0203592 A1 | 8/2009 | Beermann et al. | |
| 2009/0252729 A1 | 10/2009 | Farrington et al. | |
| 2009/0305945 A1 | 12/2009 | Wolfram et al. | |
| 2009/0318366 A1 | 12/2009 | Edens et al. | |
| 2009/0325888 A1 | 12/2009 | Edens et al. | |
| 2010/0047393 A1 | 2/2010 | Glas et al. | |
| 2010/0099607 A1 | 4/2010 | Chen | |
| 2010/0143262 A1 | 6/2010 | Valenta | |
| 2010/0256235 A1 | 10/2010 | Puder et al. | |
| 2010/0306864 A1 | 12/2010 | Tsuji et al. | |
| 2011/0177044 A1 | 7/2011 | Thomas et al. | |
| 2011/0195153 A1 | 8/2011 | Valenta et al. | |
| 2012/0071400 A1 | 3/2012 | Serizawa et al. | |
| 2012/0142588 A1 | 6/2012 | Rozing et al. | |
| 2012/0322726 A1 | 12/2012 | Somoto et al. | |

FOREIGN PATENT DOCUMENTS

| | | |
|---|---|---|
| EP | 0274939 | 7/1988 |
| EP | 0448511 | 9/1991 |
| EP | 0629350 | 12/1994 |
| EP | 0418593 | 3/1997 |
| EP | 0791357 | 8/1997 |
| EP | 2017283 | 1/2009 |
| EP | 2332428 | 6/2011 |
| WO | 9111918 | 8/1991 |
| WO | 9212711 | 8/1992 |
| WO | 9802165 | 1/1998 |
| WO | 0137850 | 5/2001 |
| WO | 0219832 | 3/2002 |
| WO | 2005027953 | 3/2005 |
| WO | 2005081628 | 9/2005 |
| WO | 2005117933 | 12/2005 |
| WO | 2006068480 | 6/2006 |
| WO | 2007060421 | 5/2007 |
| WO | 2007064208 | 6/2007 |
| WO | 2008004794 | 1/2008 |
| WO | 2008054192 | 5/2008 |
| WO | 2008056983 | 5/2008 |
| WO | 2008108651 | 9/2008 |
| WO | 2008153429 | 12/2008 |
| WO | 2009033737 | 3/2009 |
| WO | 2010043724 | 4/2010 |
| WO | 2010125192 | 11/2010 |
| WO | 2011031149 | 3/2011 |
| WO | 2011069042 | 6/2011 |
| WO | 2012143362 | 10/2012 |

OTHER PUBLICATIONS

Knip, M., et al., "Dietary Intervention in Infancy and Later Signs of Beta-Cell Autoimmunity," N Engl J Med 2010;363:1900-8.

Kondo et al., "The Response of bovine beta-lactoglobulin-specific T-cell clones to single amino acid substitution of T-cell core epitope," Pediatr. Allergy Immunol. 2008, vol. 19, pp. 592-598.

Nakajima-Adachi et al., "Determinant analysis of IgE and IgG4 antibodies and T cells specific for bovine αS1-casein from the same patients allergic to cow's milk: Existence of αS1-casein-specific B cells and T cells characteristic in cow's-milk allergy," J. Allergy Clin. Immunol. 1998; vol. 101(5), pp. 660-671).

Rosendal et al., "Detection of Potentially Allergenic Material in 12 Hydrolyzed Milk Formulas," Journal of Dairy Science 2000, vol. 83, No. 10, abstract.

Ruiter et al., "Characterization of T cell epitopes in αs1-casein in cow's milk allergic, atopic and non-atopic children," Clin. Exp. Allergy 2006, vol. 36(3), pp. 303-310.

Ruiter et al., "Role of Human Leucocyte Antigen DQ in the Presentation of T Cell Epitopes in the Major Cow's Milk Allergen αs1-casein," Int. Arch. Allergy Immunol. 2007; vol. 143(2), pp. 119-126.

Schmidt-Weber et al., "T-cell tolerance in allergic response," Allergy 2002, vol. 57, pp. 762-768.

Schulmeister et al., "Cloning, Expresion, and Mapping of Allergenic Determinants of αS1-Casein, a Major Cow's Milk Allergen," J Immunol. 2009, vol. 182(11), pp. 7019-7029.

Alles, et al., Current trends in the composition of infant milk formulas (Current Paediatrics (2004) 14, 51-63.

Brugman, S., et al., "Neonatal oral administration of DiaPep277, combined with hydrolyzed casein diet, protects against Type 1 diabetes in BB-DP rats. An experimental study," Diabetologia, vo. 47, No. 7, Jan. 1, 2004.

Brody, E., "Biological activities of bovine glycomacropeptide," British Journal of Nutrition (2000), 84, Suppl. 1, S39-S46.

Database WPI Wek 200022 Thompson Scientific, London, GB; AN 2000-251451.

Dooley, et al., http://www.medscape.comNiewarticle/449854, Dooley et al. published 2003.

Espeche Torbay, M.D., et al., "B-Casein hydrolysate generated by the cell envelope-associated proteinase of Lactobacillus delbrueckii ssp. Lactis CRL 581 protects against trinitrobenzene sulfonic acid-induced colitis in mice," J. Dairy Sci. 95:1108-1118.

Fiedorowicz, E., et al., "The influence of U-opioid receptor agonist and antagonist peptides on peripheral blood mononuclear cells (PMBCs)," Peptides 32 (2011) 707-712.

Knip, M., et al., "Dietary Intervention in Infancy and Later Signs of Beta-Cell Autoimmunity," New England Journal Medicine, vol. 363, pp. 1900-1908, Jan. 1, 2010.

Mao, X.Y., et al., "Free-radical-scavenging and anti-inflammatory effect of yak milk casein before and after enzymatic hydrolysis," Food Chemistry, vol. 126, No. 2, May 15, 2011.

MedlinePlus, Autoimmune Disorders, U.S. National Library of Medicine, accessed on Jan. 23, 2014.

Meisel, H., et al., "Bioactive peptides encrypted in milk proteins: proteolytic activation and thropho-functional properties," Antonie van Leenwenhqek 76:207-215, 1999.

Nielsen, D., et al., "Effect of milk hydrolysates on inflammation markers and drug-induced transcriptional alterations in cell-based models," J Anim Sci 2012, 90:403-405.

Requena, P., et al., "Bovine glycomacropeptide ameliorates experimental rat ileitis by mechanisms involving down regulation of interleukin 17," British Journal of Pharmacology (2008) 154, 825-832.

(56) References Cited

OTHER PUBLICATIONS

Visser, J., et al., "Potential mechanisms explaining why hydrolyzed casein-based diets outclass single amino acid-based diets in the prevention of autoimmune diabetes in diabetes-prone BB rats," Diabetes Metab Res Rev 2012;28: 505-513.

Visser, J., et al., "Restoration of impaired intestinal barrier function by hydrolysed casein diet contributes to the prevention of type 1 diabetes in the diabetes-prone BioBreeding rat," Diabetologia (2010) 53:2621-2628.

Xue-Ying, M., et al., "Free-radical-scavenging and anti-inflammatory effect of yak milk casein before and after enzymatic hydrolysis," Food Chemistry 126 (2011) 484-490.

* cited by examiner

ACTIVATING ADIPONECTIN BY CASEIN HYDROLYSATE

TECHNICAL FIELD

The present disclosure relates to a method of stimulating adiponectin using a casein hydrolysate.

BACKGROUND ART

Adiponectin (also referred to as GBP-28, apM1, AdipoQ and 30-kDa adipocyte complement-related protein (Acrp30)) is a protein which in humans is encoded by the ADIPOQ gene and is secreted by adipicytes (fat cells). It is involved in regulating glucose levels as well as fatty acid breakdown.

Adiponectin is the second best known adipokine, but in contrast to leptin, has several beneficial and protective effects. These effects include anti-inflammatory, vasculoprotective and anti-diabetic effects. Adiponectin is a 247 amino-acid protein monomer which forms trimers which further polymerize into larger polymeric complexes varying in size between 180 kDa (hexameres; LMW) or 400-600 kDa (16-meres; HMW).

Levels of adiponectin in human blood are between 5-15 µg/ml and are decreased in subjects with insulin resistance and type 2 diabetes. In general woman have a higher adiponectin plasma concentration (10-12 µg/ml) than men (7-8 µg/ml). It was also shown that adiponectin-deficient mice display diabetes. Moreover, adiponectin has been shown to promote insulin sensitivity in experimental models. Administration of adiponectin causes glucose-lowering effects and ameliorates insulin resistance. It is therefore beneficial to increase the level of adiponectin in human blood.

It has surprisingly been found that peptides selected from a casein hydrolysate activates adiponectin.

BRIEF SUMMARY

In a first aspect, the present disclosure is directed to a method for activating adiponectin by administering a composition comprising peptides selected from a casein hydrolysate.

In a second aspect, the present disclosure is directed to a method to reduce risk of heart attack by administering a composition comprising peptides selected from a casein hydrolysate.

In a further aspect, the present disclosure is directed to a method to maintain healthy weight by administering a composition comprising peptides selected from a casein hydrolysate.

In a preferred embodiment of the disclosure and/or embodiments thereof in the method of the disclosure the plasma concentration of adiponectin is increased.

In a preferred embodiment of the disclosure and/or embodiments thereof in the method of the disclosure the plasma concentration of adiponectin is adjusted to between 5-15 µg/ml. Woman have generally a higher adiponectin plasma concentration than men, and thus in a preferred embodiment the plasma concentration of adiponectin in woman is adjusted to 10-15 µg/ml, more preferably from 10-12 µg/ml, while for men the plasma concentration is preferably adjusted to 5-10 µg/ml, more preferably to 7-9 µg/ml.

In a preferred embodiment of the disclosure and/or embodiments thereof the composition comprising peptides selected from a casein hydrolysate is a nutritional composition.

In a preferred embodiment of the disclosure and/or embodiments thereof the casein hydrolysate is a cow's milk hydrolysate.

In a preferred embodiment of the disclosure and/or embodiments thereof the hydrolysate is an extensively hydrolyzed cow's milk peptide-containing hydrolysate.

In a preferred embodiment of the disclosure and/or embodiments thereof the hydrolysate consists of peptides with a molecular weight of more than 500 Da.

In a preferred embodiment of the disclosure and/or embodiments thereof the hydrolysate comprises at least one peptide selected from the group consisting of SEQ ID NO: 1-68, preferably at least 2 peptides, preferably at least 3 peptides, preferably at least 4 peptides, preferably at least 5 peptides.

In a preferred embodiment of the disclosure and/or embodiments thereof the hydrolysate comprises at least one peptide selected from the group consisting of SEQ ID NO: 1-24, preferably at least 2 peptides, preferably at least 3 peptides, preferably at least 4 peptides, preferably at least 5 peptides.

In a preferred embodiment of the disclosure and/or embodiments thereof the hydrolysate comprises at least one peptide selected from the group consisting of SEQ ID NO: 1-15, preferably at least 2 peptides, preferably at least 3 peptides, preferably at least 4 peptides, preferably at least 5 peptides.

In a preferred embodiment of the disclosure and/or embodiments thereof the hydrolysate comprises at least one peptide selected from the group consisting of SEQ ID NO: 1-12, preferably at least 2 peptides, preferably at least 3 peptides, preferably at least 4 peptides, preferably at least 5 peptides.

In a preferred embodiment of the disclosure and/or embodiments thereof the hydrolysate is administered in a nutritional composition, comprising a lipid or a fat phase, and a protein source.

In a preferred embodiment of the disclosure and/or embodiments thereof the nutritional composition comprises about 0.1 to about 1 g/100 kcal of a prebiotic composition, wherein the prebiotic composition comprises at least 20% of an oligosaccharide.

In a preferred embodiment of the disclosure and/or embodiments thereof the nutritional composition further comprises about 5 to about 100 mg/100 kcal of a source of long chain polyunsaturated fatty acids which comprises docosahexanoic acid.

In a preferred embodiment of the disclosure and/or embodiments thereof the nutritional composition further comprises arachidonic acid.

In a preferred embodiment of the disclosure and/or embodiments thereof hydrolysate is administered to human, preferably a child or juvenile.

In a preferred embodiment of the disclosure and/or embodiments thereof hydrolysate is administered to an adult.

In a preferred embodiment of the disclosure and/or embodiments thereof the human has a cow's milk allergy.

DETAILED DESCRIPTION

Figure 1:
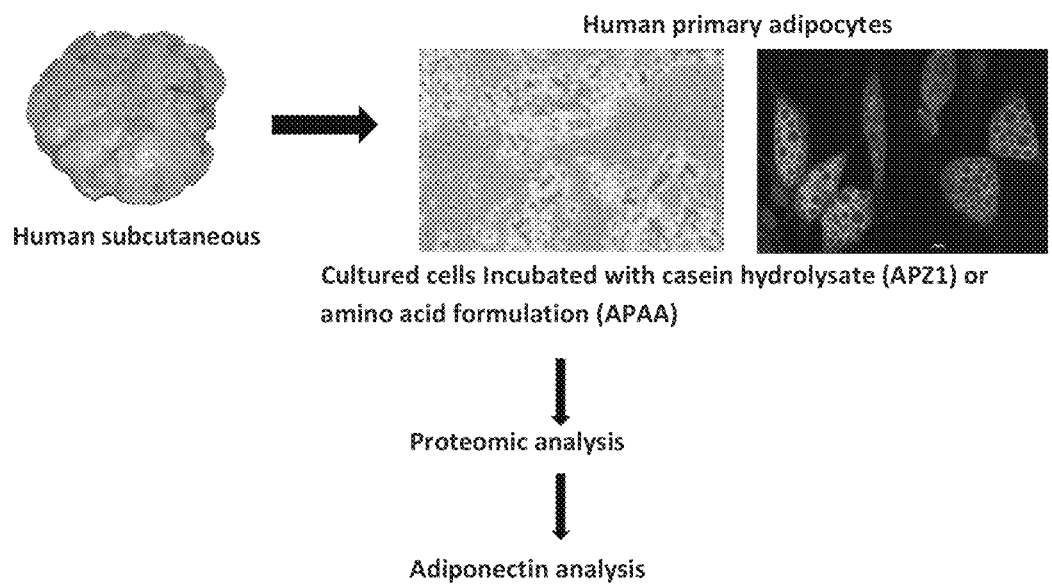
FIG. 1: Schematic representation of in vitro human adiponcectin culture assay.

The term "nutritional composition" as used herein describes a solid or liquid formulation which can therefore be eaten or drunk by a human subject for nutrition. The nutritional composition of the disclosure preferably has a nutritional value of at least 1, more preferred at least 10 and even more preferred 50 kcal (kilo calorie)/100 ml for liquid formulations and preferably at least 1, more preferred at least 10, even more preferred at least 50, such as at least 100, and most preferred at least 300 kcal/100 g for dry food formulations. In a preferred embodiment of the disclosure the nutritional formulation of the disclosure has a nutritional value of at least 50-200 kcal/100 ml for liquid formulations and at least 300-600 kcal/100 g for dry food formulations. A nutritional composition is distinguished from a vaccine. In contrast to a vaccine, a nutritional composition does not comprise any of adjuvants (unless as contaminations), activated or inactivated viral compounds (unless as contaminations), activated or inactivated bacterial compounds (unless as contaminations), and pathogenic compounds (unless as contaminations). The term "supplement" as used herein relates to a nutritional supplement which is a concentrated source of nutrient or alternatively other substances with a nutritional or physiological effect whose purpose is to supplement the normal diet.

In addition to the above recited ingredients further ingredients may be selected from lipids, minerals, carbohydrates, amino acids, amino acid chelates, anabolic nutrients, vitamins, antioxidants, probiotic bacterial strain and lipotropic agents in order to provide an optimal sustained energy and anabolic nutritional formulation. The nutritional composition may be a nutritional supplement or may provide complete nutrition. Preferably the nutritional composition is in the form of a dry food concentrate. The nutritional composition of the disclosure provides a human subject with increasing preference with at least 5%, at least 10%, at least 25%, at least 50%, at least 75% or at least 90% of the daily calorie requirement of a human subject. The person skilled in the art is well aware that the daily calorie requirement is dependent on the gender, height and age of a human subject. For example, a 30 year old male of 80 kg body weight and 180 cm height has a daily calorie requirement of around 2900 cal (calories) to maintain his body weight whereas a 30 year old female of 55 kg body weight and 165 cm height has a daily calorie requirement of around 2100 cal to maintain her body weight. In a preferred embodiment, the nutritional formulation of the present disclosure is an infant or a nutritional product for infants or juvenile.

The term "peptide" as used herein describes linear molecular chains of amino acids, including single chain molecules or their fragments. A peptide in accordance with the disclosure contains with increasing preference about 2 to 100 amino acids, about 5 to 50 amino acids, or about 5 to 40 amino acids. Peptides may further form oligomers consisting of at least two identical or different molecules. The corresponding higher order structures of such multimers are, correspondingly, termed homo- or heterodimers, homo- or heterotrimers etc. Furthermore, peptidomimetics of such peptides where amino acid(s) and/or peptide bond(s) have been replaced by functional analogs are also encompassed by the term "peptide". Such functional analogues include all known amino acids other than the 20 gene-encoded amino acids, such as selenocysteine. The term "peptide" also refers to naturally modified peptides where the modification is effected e.g. by glycosylation, acetylation, phosphorylation and similar modifications which are well known in the art. A peptide has to be distinguished from a protein in the present disclosure. A protein in accordance with the present disclosure describes an organic compound made of amino acids arranged in a linear chain and folded into a globular form. Furthermore, a protein in accordance with the present disclosure describes a chain of more than 100 amino acids. Peptides may, e.g., be produced recombinantly, (semi-) synthetically, or obtained from natural sources such as after hydrolysation of proteins, all according to methods known in the art.

The term "casein hydrolysate" as used herein defines a formula which comprises peptides derived from hydrolyzed cow's casein milk proteins. In this regard, a hydrolyzed protein is a protein that has been broken down into peptides and/or component amino acids. While there are many means of achieving protein hydrolysis, two of the most common means are prolonged boiling in a strong acid or strong base or using an enzyme such as the pancreatic protease enzyme to stimulate the naturally-occurring hydrolytic process. Hydrolysis of proteins derived from milk is preferably achieved using an enzyme or a mixture of enzyme. A casein cow milk hydrolysate can comprise peptides derived from milk, wherein the proteins of said milk have been hydrolyzed to various degrees. Accordingly, one can distinguish between a partially hydrolyzed cow's milk peptide-containing hydrolysate and an extensively hydrolyzed cow's milk peptide-containing hydrolysate. In this regard, a partially hydrolyzed cow's milk peptide-containing hydrolysate comprises more than 20% of intact cow's milk protein whereas an extensively hydrolyzed cow's milk peptide-containing hydrolysate comprises less than 1% of peptides having a size of greater than 1.5 kD. Furthermore, an extensively hydrolyzed cow's milk peptide-containing hydrolysate is preferably hypoallergenic.

The term "peptide derived from cow's milk" as used herein defines a peptide which has an amino acid sequence which is a partial amino acid sequence of a cow's milk protein. Such peptides may be obtained as outlined above by hydrolysis or may be synthesized in vitro by methods known to the skilled person and described in the examples of the disclosure.

The term "peptide-containing fraction of the hydrolysate" refers to a mixture of peptides comprising at least 2, preferably at least 5, more preferably at least 10 and most preferably at least 20 which have been isolated from the hydrolysate of the disclosure by filtration techniques which are known to the skilled person. Furthermore, techniques for the isolation of peptides from the hydrolysate of the disclosure are described herein below.

The term "child" or the term "juvenile" is used herein in accordance with the definitions provided in the art. Thus, the term "child" means a human subject between the stages of birth and the age of about 10 and the term "juvenile" means a human subject between the age of about 10 and puberty (before sexual maturity).

The term "adult" is used herein in accordance with the definitions provided in the art. Thus, this term means a human subject after puberty (after sexual maturity). A further preferred embodiment of the disclosure relates to the nutritional formulation of the disclosure, wherein the human subject has a cow's milk allergy.

The term "cow's milk allergy" describes a food allergy, i.e. an immune adverse reaction to one or more of the proteins contained in cow's milk in a human subject. The principal symptoms are gastrointestinal, dermatological and respiratory symptoms. These can translate into skin rashes, hives, vomiting, diarrhea, constipation and distress. The clinical spectrum extends to diverse disorders: anaphylactic reactions, atopic dermatitis, wheeze, infantile colic, gastro esophageal reflux disease (GERD), esophagitis, colitis gastroenteritis, headache/migraine and constipation.

The present inventors have surprisingly found that a casein hydrolysate has a beneficial effect on plasma concentration of adiponectin. Low adiponectin plasma levels are associated with type 1 diabetes, and increased weight.

It was also found that an extensively hydrolyzed cow's milk peptide-containing hydrolysate had positive effects on the plasma concentration of adiponectin. Suitable hydrolysates casein hydrolysates include casein hydrolysates. It was furthermore found that dialysis of the hydrolysate with a cut-off of 500 Da so as to include peptide sequences 500 Da and larger renders a hydrolysate fraction that has even better effect on the adiponectin plasma concentration. Accordingly, in particular embodiments, the hydrolysate comprises peptides with a molecular weight of more than 500 Da, and in further embodiments, the hydrolysate comprises peptides with a molecular weight in a range of 500 to 2000 Da. In other embodiments, the hydrolysate consists of peptides with a molecular weight of more than 500 Da, and in further embodiments, the hydrolysate consists of peptides with a molecular weight in a range of 500 to 2000 Da.

The following peptides have been identified as possibly contributing to the beneficial effect on adiponectin levels:

TABLE 1

| identified peptide in the hydrolysate: | |
| --- | --- |
| SEQ ID NO: 1* | IPNPIG |
| SEQ ID NO: 2 | IGSESTEDQ |
| SEQ ID NO 3: | DKTEIPT |
| SEQ ID NO: 4 | IVPN |
| SEQ ID NO: 5 | LEDSPE |
| SEQ ID NO: 6 | NQEQPI |
| SEQ ID NO: 7 | NVPGE |
| SEQ ID NO: 8 | PFPGPI |
| SEQ ID NO: 9 | TEDEL |
| SEQ ID NO: 10 | VPSE |
| SEQ ID NO: 11 | YPFPGP |
| SEQ ID NO: 12 | YPSGA |
| SEQ ID NO 13 | FPGPIP |
| SEQ ID NO: 14 | MHQPHQPLPPT |
| SEQ ID NO: 15 | YPFPGPIPN |
| SEQ ID NO: 16 | DMEST |
| SEQ ID NO: 17 | FPGPIPN |
| SEQ ID NO: 18 | IPNPI |
| SEQ ID NO: 19 | MESTEV |
| SEQ ID NO: 20 | PGPIPN |
| SEQ ID NO: 21 | PHQPLPPT |
| SEQ ID NO: 22 | PNPI |
| SEQ ID NO: 23 | SKDIGSE |
| SEQ ID NO: 24 | YPFPGPIP |

TABLE 1-continued

| identified peptide in the hydrolysate: | |
| --- | --- |
| SEQ ID NO: 25 | AINPSKEN |
| SEQ ID NO: 26 | APFPE |
| SEQ ID NO: 27 | DIGSES |
| SEQ ID NO: 28 | DMPI |
| SEQ ID NO: 29 | DVPS |
| SEQ ID NO: 30 | EDI |
| SEQ ID NO: 31 | ELF |
| SEQ ID NO: 32 | EMP |
| SEQ ID NO: 33 | ETAPVPL |
| SEQ ID NO: 34 | GPFP |
| SEQ ID NO: 35 | GPIV |
| SEQ ID NO: 36 | IGSSSEES |
| SEQ ID NO: 37 | IGSSSEESA |
| SEQ ID NO: 38 | INPSKE |
| SEQ ID NO: 39 | IPPLTQTPV |
| SEQ ID NO: 40 | ITAP |
| SEQ ID NO: 41 | KHQGLPQ |
| SEQ ID NO: 42 | LDVTP |
| SEQ ID NO: 43 | LPLPL |
| SEQ ID NO: 44 | NAVPI |
| SEQ ID NO: 45 | NEVEA |
| SEQ ID NO: 46 | NLL |
| SEQ ID NO: 47 | PITPT |
| SEQ ID NO: 48 | PNSLPQ |
| SEQ ID NO: 49 | PQLEIVPN |
| SEQ ID NO: 50 | PQNIPPL |
| SEQ ID NO: 51 | PVLGPV |
| SEQ ID NO: 52 | PVPQ |
| SEQ ID NO: 53 | PVVVP |
| SEQ ID NO: 54 | PVVVPP |
| SEQ ID NO: 55 | SIGSSSEESAE |
| SEQ ID NO: 56 | SISSSEE |
| SEQ ID NO: 57 | SISSSEEIVPN |
| SEQ ID NO: 58 | SPPEIN |
| SEQ ID NO: 59 | SPPEINT |
| SEQ ID NO: 60 | TDAPSFS |
| SEQ ID NO: 61 | VATEEV |
| SEQ ID NO: 62 | VLPVP |
| SEQ ID NO: 63 | VPGE |

TABLE 1-continued identified peptide in the hydrolysate:

| SEQ ID NO: 64 | VPGEIV |
| SEQ ID NO: 65 | VPITPT |
| SEQ ID NO: 66 | VVPPFLQPE |
| SEQ ID NO: 67 | VVVPP |
| SEQ ID NO: 68 | YPVEP |

In a preferred embodiment of the present disclosure and/or embodiments thereof the hydrolysate comprises a peptide with SEQ ID NO: 1 and at least one peptide selected from the group consisting of SEQ ID NO: 2-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 2 and at least one peptide selected from the group consisting of SEQ ID NO:1, and SEQ ID NO: 3-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 3 and at least one peptide selected from the group consisting of SEQ ID NO:1-2, and SEQ ID NO: 4-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 4 and at least one peptide selected from the group consisting of SEQ ID NO: 1-3, and SEQ ID NO: 5-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 5 and at least one peptide selected from the group consisting of SEQ ID NO: 1-4, and SEQ ID NO: 6-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 6 and at least one peptide selected from the group consisting of SEQ ID NO:1-5, and SEQ ID NO: 7-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 7 and at least one peptide selected from the group consisting of SEQ ID NO:1-6, and SEQ ID NO: 8-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 8 and at least one peptide selected from the group consisting of SEQ ID NO: 1-7, and SEQ ID NO: 9-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 9 and at least one peptide selected from the group consisting of SEQ ID NO: 1-8, and SEQ ID NO: 10-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 10 and at least one peptide selected from the group consisting of SEQ ID NO: 1-9, and SEQ ID NO: 11-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 11 and at least one peptide selected from the group consisting of SEQ ID NO: 1-10, and SEQ ID NO: 12-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 12 and at least one peptide selected from the group consisting of SEQ ID NO: 1-11, and SEQ ID NO: 13-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 13 and at least one peptide selected from the group consisting of SEQ ID NO: 1-12, and SEQ ID NO: 14-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 14 and at least one peptide selected from the group consisting of SEQ ID NO: 1-13, and SEQ ID NO: 15-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 15 and at least one peptide selected from the group consisting of SEQ ID NO: 1-14, and SEQ ID NO: 16-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 16 and at least one peptide selected from the group consisting of SEQ ID NO: 1-15, and SEQ ID NO: 17-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 17 and at least one peptide selected from the group consisting of SEQ ID NO: 1-16, and SEQ ID NO: 18-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 18 and at least one peptide selected from the group consisting of SEQ ID NO: 1-17, and SEQ ID NO: 19-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 19 and at least one peptide selected from the group consisting of SEQ ID NO: 1-18, and SEQ ID NO:

20-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 20 and at least one peptide selected from the group consisting of SEQ ID NO: 1-19, and SEQ ID NO: 21-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 21 and at least one peptide selected from the group consisting of SEQ ID NO: 1-20, and SEQ ID NO: 22-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 22 and at least one peptide selected from the group consisting of SEQ ID NO: 1-21, and SEQ ID NO: 23-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 23 and at least one peptide selected from the group consisting of SEQ ID NO: 1-22, and SEQ ID NO: 24-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 24 and at least one peptide selected from the group consisting of SEQ ID NO: 1-23, and SEQ ID NO: 25-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 1 and at least one peptide selected from the group consisting of SEQ ID NO: 2-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 2 and at least one peptide selected from the group consisting of SEQ ID NO: 1, and SEQ ID NO: 3-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 3 and at least one peptide selected from the group consisting of SEQ ID NO: 1-2, and SEQ ID NO: 4-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 4 and at least one peptide selected from the group consisting of SEQ ID NO: 1-3, and SEQ ID NO: 5-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 5 and at least one peptide selected from the group consisting of SEQ ID NO: 1-4, and SEQ ID NO: 6-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 6 and at least one peptide selected from the group consisting of SEQ ID NO: 1-5, and SEQ ID NO: 7-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 7 and at least one peptide selected from the group consisting of SEQ ID NO: 1-6, and SEQ ID NO: 8-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 8 and at least one peptide selected from the group consisting of SEQ ID NO: 1-7, and SEQ ID NO: 9-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 9 and at least one peptide selected from the group consisting of SEQ ID NO: 1-8, and SEQ ID NO: 10-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 10 and at least one peptide selected from the group consisting of SEQ ID NO: 1-9, and SEQ ID NO: 11-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 11 and at least one peptide selected from the group consisting of SEQ ID NO: 1-10, and SEQ ID NO: 12-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 12 and at least one peptide selected from the group consisting of SEQ ID NO: 1-11, and SEQ ID NO: 13-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 13 and at least one peptide selected from the group consisting of SEQ ID NO: 1-12, and SEQ ID NO: 14-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 14 and at least one peptide selected from the group consisting of SEQ ID NO: 1-13, and SEQ ID NO: 15-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 15 and at least one peptide selected from the group consisting of SEQ ID NO: 1-14, and SEQ ID NO:

16-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 16 and at least one peptide selected from the group consisting of SEQ ID NO: 1-15, and SEQ ID NO: 17-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 17 and at least one peptide selected from the group consisting of SEQ ID NO: 1-16, and SEQ ID NO: 18-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 18 and at least one peptide selected from the group consisting of SEQ ID NO: 1-17, and SEQ ID NO: 19-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 19 and at least one peptide selected from the group consisting of SEQ ID NO: 1-18, and SEQ ID NO: 20-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 20 and at least one peptide selected from the group consisting of SEQ ID NO: 1-19, and SEQ ID NO: 21-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 21 and at least one peptide selected from the group consisting of SEQ ID NO: 1-20, and SEQ ID NO: 22-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 22 and at least one peptide selected from the group consisting of SEQ ID NO: 1-21, and SEQ ID NO: 23-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 23 and at least one peptide selected from the group consisting of SEQ ID NO: 1-22, and SEQ ID NO: 24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 24 and at least one peptide selected from the group consisting of SEQ ID NO: 1-23, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 1 and at least one peptide selected from the group consisting of SEQ ID NO: 2-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 2 and at least one peptide selected from the group consisting of SEQ ID NO: 1, and SEQ ID NO: 3-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 3 and at least one peptide selected from the group consisting of SEQ ID NO: 1-2, and SEQ ID NO: 4-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 4 and at least one peptide selected from the group consisting of SEQ ID NO: 1-3, and SEQ ID NO: 5-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 5 and at least one peptide selected from the group consisting of SEQ ID NO: 1-4, and SEQ ID NO: 6-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 6 and at least one peptide selected from the group consisting of SEQ ID NO: 1-5, and SEQ ID NO: 7-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 7 and at least one peptide selected from the group consisting of SEQ ID NO: 1-6, and SEQ ID NO: 8-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 8 and at least one peptide selected from the group consisting of SEQ ID NO: 1-7, and SEQ ID NO: 9-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 9 and at least one peptide selected from the group consisting of SEQ ID NO: 1-8, and SEQ ID NO: 10-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 10 and at least one peptide selected from the group consisting of SEQ ID NO: 1-9, and SEQ ID NO: 11-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 11 and at least one peptide selected from the group consisting of SEQ ID NO: 1-10, and SEQ ID NO: 12-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 12 and at least one peptide selected from the group consisting of SEQ ID NO: 1-11, and SEQ ID NO: 13-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 13 and at least one peptide selected from the group consisting of SEQ ID NO: 1-12, and SEQ ID NO: 14-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 14 and at least one peptide selected from the group consisting of SEQ ID NO: 1-13, and SEQ ID NO: 15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 15 and at least one peptide selected from the group consisting of SEQ ID NO: 1-14, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 16 and at least one peptide selected from the group consisting of SEQ ID NO: 1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 17 and at least one peptide selected from the group consisting of SEQ ID NO: 1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 18 and at least one peptide selected from the group consisting of SEQ ID NO: 1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 19 and at least one peptide selected from the group consisting of SEQ ID NO: 1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 20 and at least one peptide selected from the group consisting of SEQ ID NO: 1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 21 and at least one peptide selected from the group consisting of SEQ ID NO: 1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 22 and at least one peptide selected from the group consisting of SEQ ID NO: 1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 23 and at least one peptide selected from the group consisting of SEQ ID NO: 1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 24 and at least one peptide selected from the group consisting of SEQ ID NO: 1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 1 and at least one peptide selected from the group consisting of SEQ ID NO: 2-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 2 and at least one peptide selected from the group consisting of SEQ ID NO: 1, and SEQ ID NO: 3-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 3 and at least one peptide selected from the group consisting of SEQ ID NO: 1-2, and SEQ ID NO: 4-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 4 and at least one peptide selected from the group consisting of SEQ ID NO: 1-3, and SEQ ID NO: 5-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 5 and at least one peptide selected from the group consisting of SEQ ID NO: 1-4, and SEQ ID NO: 6-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 6 and at least one peptide selected from the group consisting of SEQ ID NO: 1-5, and SEQ ID NO: 7-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 7 and at least one peptide selected from the group consisting of SEQ ID NO: 1-6, and SEQ ID NO: 8-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 8 and at least one peptide selected from the group consisting of SEQ ID NO: 1-7, and SEQ ID NO: 9-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 9 and at least one peptide selected from the group consisting of SEQ ID NO: 1-8, and SEQ ID NO: 10-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 10 and at least one peptide selected from the group consisting of SEQ ID NO: 1-9, and SEQ ID NO: 11-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 11 and at least one peptide selected from the group consisting of SEQ ID NO: 1-10, and SEQ ID NO: 12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 12 and at least one peptide selected from the group consisting of SEQ ID NO: 1-11, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 13 and at least one peptide selected from the group consisting of SEQ ID NO: 1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 14 and at least one peptide selected from the group consisting of SEQ ID NO: 1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 15 and at least one peptide selected from the group consisting of SEQ ID NO: 1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 16 and at least one peptide selected from the group consisting of SEQ ID NO: 1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 17 and at least one peptide selected from the group consisting of SEQ ID NO: 1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 18 and at least one peptide selected from the group consisting of SEQ ID NO: 1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 19 and at least one peptide selected from the group consisting of SEQ ID NO: 1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 20 and at least one peptide selected from the group consisting of SEQ ID NO: 1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 21 and at least one peptide selected from the group consisting of SEQ ID NO: 1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 22 and at least one peptide selected from the group consisting of SEQ ID NO: 1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 23 and at least one peptide selected from the group consisting of SEQ ID NO: 1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 24 and at least one peptide selected from the group consisting of SEQ ID NO: 1-12, preferably at least 2 peptides, preferably at least 3 peptides, preferably at least 4 peptides, preferably at least 5 peptides.

In a preferred embodiment of the present disclosure and/or embodiments thereof the hydrolysate is a hydrolysate comprising combinations of SEQ ID NO: 1, and SEQ ID NO: 2.

In a preferred embodiment of the present disclosure and/or embodiments thereof the hydrolysate is a hydrolysate comprising combinations of SEQ ID NO: 1, and SEQ ID NO: 3.

In a preferred embodiment of the present disclosure and/or embodiments thereof the hydrolysate is a hydrolysate comprising combinations of SEQ ID NO: 1, and SEQ ID NO: 4.

In a preferred embodiment of the present disclosure and/or embodiments thereof the hydrolysate is a hydrolysate comprising combinations of SEQ ID NO: 1, and SEQ ID NO: 5.

In a preferred embodiment of the present disclosure and/or embodiments thereof the hydrolysate is a hydrolysate comprising combinations of SEQ ID NO: 1, and SEQ ID NO: 6.

In a preferred embodiment of the present disclosure and/or embodiments thereof the hydrolysate is a hydrolysate comprising combinations of SEQ ID NO: 1, and SEQ ID NO: 7.

In a preferred embodiment of the present disclosure and/or embodiments thereof the hydrolysate is a hydrolysate comprising combinations of SEQ ID NO: 1, and SEQ ID NO: 8.

In a preferred embodiment of the present disclosure and/or embodiments thereof the hydrolysate is a hydrolysate comprising combinations of SEQ ID NO: 1, and SEQ ID NO: 9.

In a preferred embodiment of the present disclosure and/or embodiments thereof the hydrolysate is a hydrolysate comprising combinations of SEQ ID NO: 1, and SEQ ID NO: 10.

In a preferred embodiment of the present disclosure and/or embodiments thereof the hydrolysate is a hydrolysate comprising combinations of SEQ ID NO: 1, and SEQ ID NO: 11.

In a preferred embodiment of the present disclosure and/or embodiments thereof the hydrolysate is a hydrolysate comprising combinations of SEQ ID NO: 1, and SEQ ID NO: 12.

In a preferred embodiment of the present disclosure and/or embodiments thereof the hydrolysate is a hydrolysate comprising combinations of SEQ ID NO: 1, and SEQ ID NO: 13.

In a preferred embodiment of the present disclosure and/or embodiments thereof the hydrolysate is a hydrolysate comprising combinations of SEQ ID NO: 1, and SEQ ID NO: 14.

In a preferred embodiment of the present disclosure and/or embodiments thereof the hydrolysate is a hydrolysate comprising combinations of SEQ ID NO: 1, and SEQ ID NO: 15.

In a preferred embodiment of the present disclosure and/or embodiments thereof the hydrolysate is a hydrolysate comprising combinations of SEQ ID NO: 1, and SEQ ID NO: 16.

In a preferred embodiment of the present disclosure and/or embodiments thereof the hydrolysate is a hydrolysate comprising combinations of SEQ ID NO: 1, and SEQ ID NO: 17.

In a preferred embodiment of the present disclosure and/or embodiments thereof the hydrolysate is a hydrolysate comprising combinations of SEQ ID NO: 1, and SEQ ID NO: 18.

In a preferred embodiment of the present disclosure and/or embodiments thereof the hydrolysate is a hydrolysate comprising combinations of SEQ ID NO: 1, and SEQ ID NO: 19.

In a preferred embodiment of the present disclosure and/or embodiments thereof the hydrolysate is a hydrolysate comprising combinations of SEQ ID NO: 1, and SEQ ID NO: 20.

In a preferred embodiment of the present disclosure and/or embodiments thereof the hydrolysate is a hydrolysate comprising combinations of SEQ ID NO: 1, and SEQ ID NO: 21.

In a preferred embodiment of the present disclosure and/or embodiments thereof the hydrolysate is a hydrolysate comprising combinations of SEQ ID NO: 1, and SEQ ID NO: 22.

In a preferred embodiment of the present disclosure and/or embodiments thereof the hydrolysate is a hydrolysate comprising combinations of SEQ ID NO: 1, and SEQ ID NO: 23.

In a preferred embodiment of the present disclosure and/or embodiments thereof the hydrolysate is a hydrolysate comprising combinations of SEQ ID NO: 1, and SEQ ID NO: 24.

In a preferred embodiment of the disclosure and/or embodiments thereof the nutritional formulation additionally comprises one or more of carbohydrates, nucleic acids, lipids, minerals, anabolic nutrients, vitamins, antioxidants, probiotic bacterial strains and lipotropic agents.

In a preferred embodiment of the present disclosure and/or embodiments thereof the nutritional composition comprises a fat phase wherein the lipid or fat is present at a level of up to about 7 g/100 kcal.

In a preferred embodiment of the present disclosure and/or embodiments thereof the nutritional composition wherein the protein source is present at a level of up to about 5 g/100 kcal.

In a preferred embodiment of the present disclosure and/or embodiments thereof the nutritional composition comprises an oligosaccharide wherein the oligosaccharide comprises galacto-oligosaccharide.

In a preferred embodiment of the present disclosure and/or embodiments thereof the nutritional composition further comprises polydextrose.

The present disclosure is also directed to a peptide-containing fraction of a casein hydrolysate for use in activating adiponectin.

The present is also directed to peptides selected from a casein hydrolysate for use in maintaining healthy weight, by administering a composition comprising peptides selected from a casein hydrolysate.

The present is also directed to peptides selected from a casein hydrolysate for use in reducing the risk of heart attack by administering a composition comprising peptides selected from a casein hydrolysate.

In a preferred embodiment of the present disclosure and/or embodiments thereof the plasma concentration of adiponectin is increased. Preferably the plasma concentration of adiponectin is adjusted to between 5-10 mg/ml.

In a preferred embodiment of the present disclosure and/or embodiments thereof the composition comprising peptides selected from a casein hydrolysate is a nutritional composition.

In a preferred embodiment of the present disclosure and/or embodiments thereof the casein hydrolysate is a cow's milk hydrolysate.

In a preferred embodiment of the present disclosure and/or embodiments thereof the hydrolysate is an extensively hydrolyzed cow's milk peptide-containing hydrolysate.

The preferred embodiments of the method of the disclosure and/or embodiments thereof are also preferred embodiments of the casein hydrolysate for use in activating adiponectin, for use in maintaining healthy weight, and/or for use in reducing the risk of heart attack.

The disclosure is now exemplified by the following non limiting examples.

Examples

Adipocyte Isolation and Culture

Subcutaneous adipose tissue was obtained from healthy lean or moderately overweight women undergoing plastic surgery. The procedure was approved by the ethical committee of the Heinrich-Heine-University (Düsseldorf, Germany). Preadipocytes were isolated by collagenase digestion. Isolated cell pellets were resuspended in DMEM/F12 medium supplemented with 10% FCS, seeded in six-well or 12-well culture dishes, respectively, and maintained at 37° C. with 5% $CO_2$. After reaching confluence (day 0 of differentiation), cell cultures were incubated incubated in an adipocyte differentiation medium (DMEM/F12, 33 mM biotin, 17 mmol/l d-panthothenic-acid, 66 nM insulin, 1 nM triiodo-L-thyronine, 100 nM cortisol, 10 mg/ml apo-transferrin, 50 mg/ml gentamycin, 0.25 mg/ml amphotericin B, 15 mM HEPES, 14 nM $NaHCO_3$, pH 7.4) with troglitazone (5 0\4) for 3 days. Once differentiation was started the cells were further incubated in adipocyte differentiation medium with medium changes every 2-3 days for a total differentiation period of 14 days.

After the differentiation period (14 days), the adipocytes were challenged with extensive casein hydrolysate at different concentrations (0.01%, 0.1% and 1%, respectively) for 24 h. See FIG. 1 for a schematic overview of the in vitro human primary adipocyte cultures assay.

Adiponectin Release Upon Casein Hydrolysate Stimulation

The isolated human preadipocytes were carefully counted and the same cell number per well was plated. After the differentiation period, the cells are treated with casein hydrolysate at 0.01%, 0.1% and 1%. After 24 h, the supernatants were collected and stored at −20° C. for analysis of adipokine content with an ELISA kit.

The ELISA kits includes a plate with wells that are coated with a primary antibody against human adiponectin. The supernatants are added and after the appropriate incubation time, the sample is washed so that only the adipokine bound to the antibody is left. Another buffer containing the secondary antibody conjugated with HRP is added to the wells. After the indicated incubation time, the excess of secondary antibody is removed by washing and the remaining HRP bound to the adipokine-antibody complex reacts when adding the TMB buffer. The reaction is stopped by adding an acidic solution and the reacting yellow colour is measured. The absorbance is proportional to the yellow colour which indicates the presence of the adipokine of interest. A standard curve is obtained by plotting the concentration of the standards versus their absorbances, interpolating from the standard curve the concentration of adipokine in the sample is calculated.

The kits included a standard of human recombinant adiponectin used to calculate the adiponectin concentration. Moreover, the kits include a Quality control high and low standards with known concentrations. The kit for adiponectin ELISA recognizes natural and recombinant human adiponectin (full length, mutation-modified trimer only forming and globular domain).

Once the incubation conditions were validated, and unspecific effects of the milk fractions alone were discarded, we assessed the adiponectin secretion in the supernatants of the adipocytes previously stimulated with casein hydrolysate.

Figure 2:
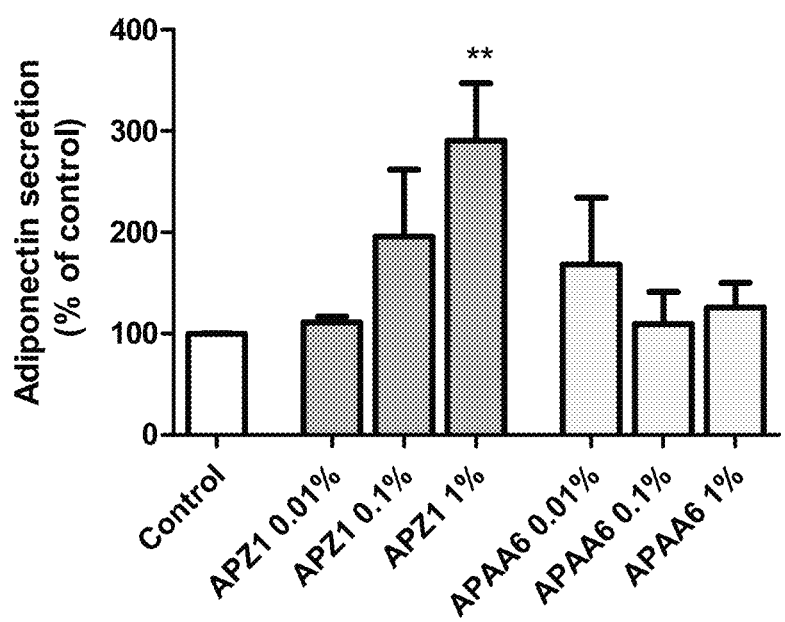
FIG. 2 Results of adiponectin secretion of adipocytes upon stimulation of hydrolysate (APZ1) or single acid amino acid mixture (APAA6).

A casein hydrolysate of the present disclosure (APZ1) triggered a significant upregulation of adiponectin secretion at 1%. (290.6±56.6% vs. control, see figure), following a dose-dependent trend. The effect of the APZ1 fraction is independent of an single amino acid mixture (APAA6), the latter did not exert any significant effect on adiponectin secretion. See FIG. 2 showing the results of adiponectin secretion of adipocytes upon stimulation of hydrolasate (APZ1) or single acid amino acid mixture (APAA6).

What is claimed is:

1. A method for promoting healthy weight in a subject by administering a composition comprising a casein hydrolysate to the subject, wherein the hydrolysate consists of peptides with a molecular weight of more than 500 Da, wherein the hydrolysate comprises at least three peptides selected from the group consisting of SEQ ID NO: 1-68, and wherein the plasma concentration of adiponectin in the subject is increased upon administration of the composition.

2. The method according to claim 1 wherein the plasma concentration of adiponectin is adjusted to between 5-15 μg/ml.

3. The method according to claim 1 wherein the hydrolysate comprises at least three peptides selected from the group consisting of SEQ ID NO: 1-24.

4. The method according to claim 3 wherein the hydrolysate comprises at least three peptide selected from the group consisting of SEQ ID NO: 1-15.

5. The method according to claim 1 wherein the hydrolysate comprises a peptide with SEQ ID NO: 1 and at least three peptides selected from the group consisting of SEQ ID NO: 2-68.

6. The method according to claim 1 wherein the hydrolysate is administered in a nutritional composition, comprising a lipid or a fat phase, and a protein source.

7. The method according to claim 6 wherein the nutritional composition comprises about 0.1 to about 1 g/100 kcal of a prebiotic composition, wherein the prebiotic composition comprises at least 20% of an oligosaccharide.

8. The method according to claim 6 wherein the nutritional composition further comprises about 5 to about 100 mg/100 kcal of a source of long chain polyunsaturated fatty acids which comprises docosahexaenoic acid.

9. The method according to claim 8 wherein the nutritional composition further comprises arachidonic acid.

10. The method according to claim 1 wherein the subject is a human child or juvenile.

11. The method according to claim 1 wherein the nutritional formulation additionally comprises one or more of carbohydrates, nucleic acids, lipids, minerals, anabolic nutrients, vitamins, antioxidants, probiotic bacterial strains and lipotropic agents.

12. The method according to claim 1, wherein the hydrolysate comprises at least three peptides selected from the group consisting of SEQ ID NO: 1-3, 5-9, 11-21, and 23-68.

13. The method of claim 1, wherein the hydrolysate consists of peptides having a molecular weight in a range of 500 Da to 2000 Da.

* * * * *

```
                        SEQUENCE LISTING

<160> NUMBER OF SEQ ID NOS: 68

<210> SEQ ID NO 1
<211> LENGTH: 6
<212> TYPE: PRT
<213> ORGANISM: BOVINE

<400> SEQUENCE: 1

Ile Pro Asn Pro Ile Gly
1               5

<210> SEQ ID NO 2
<211> LENGTH: 9
<212> TYPE: PRT
<213> ORGANISM: BOVINE

<400> SEQUENCE: 2

Ile Gly Ser Glu Ser Thr Glu Asp Gln
1               5

<210> SEQ ID NO 3
<211> LENGTH: 7
<212> TYPE: PRT
<213> ORGANISM: BOVINE

<400> SEQUENCE: 3

Asp Lys Thr Glu Ile Pro Thr
1               5

<210> SEQ ID NO 4
<211> LENGTH: 4
<212> TYPE: PRT
<213> ORGANISM: BOVINE

<400> SEQUENCE: 4

Ile Val Pro Asn
1

<210> SEQ ID NO 5
<211> LENGTH: 6
<212> TYPE: PRT
<213> ORGANISM: BOVINE

<400> SEQUENCE: 5

Leu Glu Asp Ser Pro Glu
1               5

<210> SEQ ID NO 6
<211> LENGTH: 6
<212> TYPE: PRT
<213> ORGANISM: BOVINE
```

```
<400> SEQUENCE: 6

Asn Gln Glu Gln Pro Ile
1               5

<210> SEQ ID NO 7
<211> LENGTH: 5
<212> TYPE: PRT
<213> ORGANISM: BOVINE

<400> SEQUENCE: 7

Asn Val Pro Gly Glu
1               5

<210> SEQ ID NO 8
<211> LENGTH: 6
<212> TYPE: PRT
<213> ORGANISM: BOVINE

<400> SEQUENCE: 8

Pro Phe Pro Gly Pro Ile
1               5

<210> SEQ ID NO 9
<211> LENGTH: 5
<212> TYPE: PRT
<213> ORGANISM: BOVINE

<400> SEQUENCE: 9

Thr Glu Asp Glu Leu
1               5

<210> SEQ ID NO 10
<211> LENGTH: 4
<212> TYPE: PRT
<213> ORGANISM: BOVINE

<400> SEQUENCE: 10

Val Pro Ser Glu
1

<210> SEQ ID NO 11
<211> LENGTH: 6
<212> TYPE: PRT
<213> ORGANISM: BOVINE

<400> SEQUENCE: 11

Tyr Pro Phe Pro Gly Pro
1               5

<210> SEQ ID NO 12
<211> LENGTH: 5
<212> TYPE: PRT
<213> ORGANISM: BOVINE

<400> SEQUENCE: 12

Tyr Pro Ser Gly Ala
1               5

<210> SEQ ID NO 13
<211> LENGTH: 6
<212> TYPE: PRT
<213> ORGANISM: BOVINE

<400> SEQUENCE: 13
```

Phe Pro Gly Pro Ile Pro
1               5

<210> SEQ ID NO 14
<211> LENGTH: 11
<212> TYPE: PRT
<213> ORGANISM: BOVINE

<400> SEQUENCE: 14

Met His Gln Pro His Gln Pro Leu Pro Pro Thr
1               5                   10

<210> SEQ ID NO 15
<211> LENGTH: 9
<212> TYPE: PRT
<213> ORGANISM: BOVINE

<400> SEQUENCE: 15

Tyr Pro Phe Pro Gly Pro Ile Pro Asn
1               5

<210> SEQ ID NO 16
<211> LENGTH: 5
<212> TYPE: PRT
<213> ORGANISM: BOVINE

<400> SEQUENCE: 16

Asp Met Glu Ser Thr
1               5

<210> SEQ ID NO 17
<211> LENGTH: 7
<212> TYPE: PRT
<213> ORGANISM: BOVINE

<400> SEQUENCE: 17

Phe Pro Gly Pro Ile Pro Asn
1               5

<210> SEQ ID NO 18
<211> LENGTH: 5
<212> TYPE: PRT
<213> ORGANISM: BOVINE

<400> SEQUENCE: 18

Ile Pro Asn Pro Ile
1               5

<210> SEQ ID NO 19
<211> LENGTH: 6
<212> TYPE: PRT
<213> ORGANISM: BOVINE

<400> SEQUENCE: 19

Met Glu Ser Thr Glu Val
1               5

<210> SEQ ID NO 20
<211> LENGTH: 6
<212> TYPE: PRT
<213> ORGANISM: BOVINE

<400> SEQUENCE: 20

Pro Gly Pro Ile Pro Asn
1               5

```
<210> SEQ ID NO 21
<211> LENGTH: 8
<212> TYPE: PRT
<213> ORGANISM: BOVINE

<400> SEQUENCE: 21

Pro His Gln Pro Leu Pro Pro Thr
1               5

<210> SEQ ID NO 22
<211> LENGTH: 4
<212> TYPE: PRT
<213> ORGANISM: BOVINE

<400> SEQUENCE: 22

Pro Asn Pro Ile
1

<210> SEQ ID NO 23
<211> LENGTH: 7
<212> TYPE: PRT
<213> ORGANISM: BOVINE

<400> SEQUENCE: 23

Ser Lys Asp Ile Gly Ser Glu
1               5

<210> SEQ ID NO 24
<211> LENGTH: 8
<212> TYPE: PRT
<213> ORGANISM: BOVINE

<400> SEQUENCE: 24

Tyr Pro Phe Pro Gly Pro Ile Pro
1               5

<210> SEQ ID NO 25
<211> LENGTH: 8
<212> TYPE: PRT
<213> ORGANISM: BOVINE

<400> SEQUENCE: 25

Ala Ile Asn Pro Ser Lys Glu Asn
1               5

<210> SEQ ID NO 26
<211> LENGTH: 5
<212> TYPE: PRT
<213> ORGANISM: BOVINE

<400> SEQUENCE: 26

Ala Pro Phe Pro Glu
1               5

<210> SEQ ID NO 27
<211> LENGTH: 6
<212> TYPE: PRT
<213> ORGANISM: BOVINE

<400> SEQUENCE: 27

Asp Ile Gly Ser Glu Ser
1               5
```

```
<210> SEQ ID NO 28
<211> LENGTH: 4
<212> TYPE: PRT
<213> ORGANISM: BOVINE

<400> SEQUENCE: 28

Asp Met Pro Ile
1

<210> SEQ ID NO 29
<211> LENGTH: 4
<212> TYPE: PRT
<213> ORGANISM: BOVINE

<400> SEQUENCE: 29

Asp Val Pro Ser
1

<210> SEQ ID NO 30
<211> LENGTH: 3
<212> TYPE: PRT
<213> ORGANISM: BOVINE

<400> SEQUENCE: 30

Glu Asp Ile
1

<210> SEQ ID NO 31
<211> LENGTH: 3
<212> TYPE: PRT
<213> ORGANISM: BOVINE

<400> SEQUENCE: 31

Glu Leu Phe
1

<210> SEQ ID NO 32
<211> LENGTH: 3
<212> TYPE: PRT
<213> ORGANISM: BOVINE

<400> SEQUENCE: 32

Glu Met Pro
1

<210> SEQ ID NO 33
<211> LENGTH: 7
<212> TYPE: PRT
<213> ORGANISM: BOVINE

<400> SEQUENCE: 33

Glu Thr Ala Pro Val Pro Leu
1               5

<210> SEQ ID NO 34
<211> LENGTH: 4
<212> TYPE: PRT
<213> ORGANISM: BOVINE

<400> SEQUENCE: 34

Gly Pro Phe Pro
1

<210> SEQ ID NO 35
<211> LENGTH: 4
```

```
<212> TYPE: PRT
<213> ORGANISM: BOVINE

<400> SEQUENCE: 35

Gly Pro Ile Val
1

<210> SEQ ID NO 36
<211> LENGTH: 8
<212> TYPE: PRT
<213> ORGANISM: BOVINE

<400> SEQUENCE: 36

Ile Gly Ser Ser Ser Glu Glu Ser
1               5

<210> SEQ ID NO 37
<211> LENGTH: 9
<212> TYPE: PRT
<213> ORGANISM: BOVINE

<400> SEQUENCE: 37

Ile Gly Ser Ser Ser Glu Glu Ser Ala
1               5

<210> SEQ ID NO 38
<211> LENGTH: 6
<212> TYPE: PRT
<213> ORGANISM: BOVINE

<400> SEQUENCE: 38

Ile Asn Pro Ser Lys Glu
1               5

<210> SEQ ID NO 39
<211> LENGTH: 9
<212> TYPE: PRT
<213> ORGANISM: BOVINE

<400> SEQUENCE: 39

Ile Pro Pro Leu Thr Gln Thr Pro Val
1               5

<210> SEQ ID NO 40
<211> LENGTH: 4
<212> TYPE: PRT
<213> ORGANISM: BOVINE

<400> SEQUENCE: 40

Ile Thr Ala Pro
1

<210> SEQ ID NO 41
<211> LENGTH: 7
<212> TYPE: PRT
<213> ORGANISM: BOVINE

<400> SEQUENCE: 41

Lys His Gln Gly Leu Pro Gln
1               5

<210> SEQ ID NO 42
<211> LENGTH: 5
<212> TYPE: PRT
<213> ORGANISM: BOVINE
```

<400> SEQUENCE: 42

Leu Asp Val Thr Pro
1               5

<210> SEQ ID NO 43
<211> LENGTH: 5
<212> TYPE: PRT
<213> ORGANISM: BOVINE

<400> SEQUENCE: 43

Leu Pro Leu Pro Leu
1               5

<210> SEQ ID NO 44
<211> LENGTH: 5
<212> TYPE: PRT
<213> ORGANISM: BOVINE

<400> SEQUENCE: 44

Asn Ala Val Pro Ile
1               5

<210> SEQ ID NO 45
<211> LENGTH: 5
<212> TYPE: PRT
<213> ORGANISM: BOVINE

<400> SEQUENCE: 45

Asn Glu Val Glu Ala
1               5

<210> SEQ ID NO 46
<211> LENGTH: 3
<212> TYPE: PRT
<213> ORGANISM: BOVINE

<400> SEQUENCE: 46

Asn Leu Leu
1

<210> SEQ ID NO 47
<211> LENGTH: 5
<212> TYPE: PRT
<213> ORGANISM: BOVINE

<400> SEQUENCE: 47

Pro Ile Thr Pro Thr
1               5

<210> SEQ ID NO 48
<211> LENGTH: 6
<212> TYPE: PRT
<213> ORGANISM: BOVINE

<400> SEQUENCE: 48

Pro Asn Ser Leu Pro Gln
1               5

<210> SEQ ID NO 49
<211> LENGTH: 6
<212> TYPE: PRT
<213> ORGANISM: BOVINE

<400> SEQUENCE: 49

Pro Asn Ser Leu Pro Gln
1               5

<210> SEQ ID NO 50
<211> LENGTH: 7
<212> TYPE: PRT
<213> ORGANISM: BOVINE

<400> SEQUENCE: 50

Pro Gln Asn Ile Pro Pro Leu
1               5

<210> SEQ ID NO 51
<211> LENGTH: 6
<212> TYPE: PRT
<213> ORGANISM: BOVINE

<400> SEQUENCE: 51

Pro Val Leu Gly Pro Val
1               5

<210> SEQ ID NO 52
<211> LENGTH: 4
<212> TYPE: PRT
<213> ORGANISM: BOVINE

<400> SEQUENCE: 52

Pro Val Pro Gln
1

<210> SEQ ID NO 53
<211> LENGTH: 5
<212> TYPE: PRT
<213> ORGANISM: BOVINE

<400> SEQUENCE: 53

Pro Val Val Val Pro
1               5

<210> SEQ ID NO 54
<211> LENGTH: 6
<212> TYPE: PRT
<213> ORGANISM: BOVINE

<400> SEQUENCE: 54

Pro Val Val Val Pro Pro
1               5

<210> SEQ ID NO 55
<211> LENGTH: 11
<212> TYPE: PRT
<213> ORGANISM: BOVINE

<400> SEQUENCE: 55

Ser Ile Gly Ser Ser Ser Glu Glu Ser Ala Glu
1               5                   10

<210> SEQ ID NO 56
<211> LENGTH: 7
<212> TYPE: PRT
<213> ORGANISM: BOVINE

<400> SEQUENCE: 56

Ser Ile Ser Ser Ser Glu Glu

```
<210> SEQ ID NO 57
<211> LENGTH: 11
<212> TYPE: PRT
<213> ORGANISM: BOVINE

<400> SEQUENCE: 57

Ser Ile Ser Ser Ser Glu Glu Ile Val Pro Asn
1               5                   10

<210> SEQ ID NO 58
<211> LENGTH: 6
<212> TYPE: PRT
<213> ORGANISM: BOVINE

<400> SEQUENCE: 58

Ser Pro Pro Glu Ile Asn
1               5

<210> SEQ ID NO 59
<211> LENGTH: 7
<212> TYPE: PRT
<213> ORGANISM: BOVINE

<400> SEQUENCE: 59

Ser Pro Pro Glu Ile Asn Thr
1               5

<210> SEQ ID NO 60
<211> LENGTH: 7
<212> TYPE: PRT
<213> ORGANISM: BOVINE

<400> SEQUENCE: 60

Thr Asp Ala Pro Ser Phe Ser
1               5

<210> SEQ ID NO 61
<211> LENGTH: 6
<212> TYPE: PRT
<213> ORGANISM: BOVINE

<400> SEQUENCE: 61

Val Ala Thr Glu Glu Val
1               5

<210> SEQ ID NO 62
<211> LENGTH: 5
<212> TYPE: PRT
<213> ORGANISM: BOVINE

<400> SEQUENCE: 62

Val Leu Pro Val Pro
1               5

<210> SEQ ID NO 63
<211> LENGTH: 4
<212> TYPE: PRT
<213> ORGANISM: BOVINE

<400> SEQUENCE: 63

Val Pro Gly Glu
1
```

```
<210> SEQ ID NO 64
<211> LENGTH: 6
<212> TYPE: PRT
<213> ORGANISM: BOVINE

<400> SEQUENCE: 64

Val Pro Gly Glu Ile Val
1               5

<210> SEQ ID NO 65
<211> LENGTH: 6
<212> TYPE: PRT
<213> ORGANISM: BOVINE

<400> SEQUENCE: 65

Val Pro Ile Thr Pro Thr
1               5

<210> SEQ ID NO 66
<211> LENGTH: 9
<212> TYPE: PRT
<213> ORGANISM: BOVINE

<400> SEQUENCE: 66

Val Val Pro Pro Phe Leu Gln Pro Glu
1               5

<210> SEQ ID NO 67
<211> LENGTH: 5
<212> TYPE: PRT
<213> ORGANISM: BOVINE

<400> SEQUENCE: 67

Val Val Val Pro Pro
1               5

<210> SEQ ID NO 68
<211> LENGTH: 5
<212> TYPE: PRT
<213> ORGANISM: BOVINE

<400> SEQUENCE: 68

Tyr Pro Val Glu Pro
1               5
```